United States Patent
Feist et al.

(10) Patent No.: US 10,927,063 B2
(45) Date of Patent: Feb. 23, 2021

(54) PROCESS FOR THE PREPARATION OF HALOGENATED CARBOXYLIC ANHYDRIDES

(71) Applicant: SOLVAY SA, Brussels (BE)

(72) Inventors: Heinz Rudi Feist, Issum (DE); Werner Rudolph, Hannover (DE)

(73) Assignee: SOLVAY SA, Brussels (BE)

( * ) Notice: Subject to any disclaimer, the term of this patent is extended or adjusted under 35 U.S.C. 154(b) by 0 days.

(21) Appl. No.: 14/896,086

(22) PCT Filed: Aug. 5, 2014

(86) PCT No.: PCT/IB2014/063713
§ 371 (c)(1),
(2) Date: Dec. 4, 2015

(87) PCT Pub. No.: WO2014/195929
PCT Pub. Date: Dec. 11, 2014

(65) Prior Publication Data
US 2016/0122273 A1 May 5, 2016

(30) Foreign Application Priority Data
Jun. 6, 2013 (EP) ..................................... 13170868

(51) Int. Cl.
*C07C 51/56* (2006.01)
*C07C 51/573* (2006.01)

(52) U.S. Cl.
CPC ............ *C07C 51/56* (2013.01); *C07C 51/573* (2013.01)

(58) Field of Classification Search
CPC ......... C07C 51/56; C07C 53/16; C07C 53/18; C07C 51/573
USPC ....................................................... 562/895
See application file for complete search history.

(56) References Cited

U.S. PATENT DOCUMENTS

| | | | |
|---|---|---|---|
| 2,628,253 A * | 2/1953 | Dowdall ............... | C07C 305/06 562/36 |
| 3,576,888 A | 4/1971 | Lichstein et al. | |
| 4,038,310 A * | 7/1977 | Bjornson ............. | C07C 51/487 205/430 |
| 8,119,655 B2 | 2/2012 | Dong et al. | |
| 2010/0234340 A1 | 9/2010 | Schunk et al. | |
| 2011/0065955 A1* | 3/2011 | Metz ....................... | C07C 51/04 562/605 |

FOREIGN PATENT DOCUMENTS

| | | | |
|---|---|---|---|
| CN | 101108797 A | | 1/2008 |
| DE | 590237 C | | 1/1934 |
| IN | 2011DE03339 | * | 5/2013 |
| JP | 2011093808 A | | 5/2011 |

OTHER PUBLICATIONS

Amat ("Thermolysis of Unsaturated Dicarboxylic Acids in Sulfuric Acid and Oleum. A Comparison with the CIMS Fragmentation Patterns" J. Org. Chem. 1988, 53, 5480-5484).*
Stichlmair ("Distillation, 2. Equipment" Ullmann's Encyclopedia of Industrial Chemistry, 2010, p. 455-475).*
Foster ("Sulfonation and Sulfation Processes" downloaded from http://www.chemithon.com/Resources/pdfs/Technical_papers/Sulfo%20and%20Sulfa%201.pdf on Apr. 25, 2018, dated 1997, p. 1-36).*
Francis ("The performance of stainless steels in concentrated sulphuric acid" downloaded from https://www.rolledalloys.com/shared/library/technical-papers/corrosive/The-Performance-of-Stainless-Steels-in-Concentrated-Sulfuric-Acid.pdf on Apr. 25, 2018, dated Nov. 2009, p. 1-4).*
Tojo ("Practical synthesis of gem-difluorides from cyclohexanone: Synthesis of gem-bistrifluoroacetate and their reactions with flouride nucleophiles" Journal of Flourine Chemistry, 131, 2010, p. 29-35) (Year: 2010).*
SDS data sheet for chlorodifluoroacetic acid (Anpel, downloaded from http://www.anpel.com.cn/UpFile/Stock/201508/MSDS-4.431000EN.pdf on Jan. 18, 2019) (Year: 2019).*
Milos Hudlicky, "Chemistry of Organic Fluorine Compounds", 2nd (Revised) Edition, A laboratory manual with comprehensive literature coverage, 1976, p. 726.
K.H. Buchel, et al. eds. Methoden der Organischen Chemie (Houben-Weyl). Georg Thieme Verlag : Stuttgart. p. 634, 1985.
Anpel Laboratory Technologies (Shanghai) Inc., "Trifluoroacetic Acid", Product No. 4.018443, Version No. 51.1.1, CNW Technologies Safety Data Sheet, Revision Date Jan. 1, 2013, 14 pages.
Ana M. Amat, et al. "Modified Photobehavior of Carboxylic Acid Derivatives Induced by Protonation" Tetrahedron (1987) vol. 43, No. 5, pp. 905-910.
Anne Marie Helmenstine "List of the Strong Acids" dated Jul. 3, 2019, downloaded from https://www.thoughtco.com on Oct. 2, 2020.
Alexander Shmailov, et al. "First synthesis of a-(3-R-1-adamantyl)sulfoacetic acids and their derivatives" Tetrahedron (2012), 68, 4765-4772.

* cited by examiner

*Primary Examiner* — Amy C Bonaparte

(57) ABSTRACT

The present invention relates to a process for the preparation of halogenated carboxylic anhydrides, e.g. for the preparation of trifluoroacetic anhydride. The preparation is achieved by reacting a halogenated carboxylic acid, e.g. trifluoroacetic acid, with sulfuric acid, oleum and/or disulfuric acid.

14 Claims, No Drawings

PROCESS FOR THE PREPARATION OF HALOGENATED CARBOXYLIC ANHYDRIDES

This application is a U.S. national stage entry under 35 U.S.C. § 371 of International Application No. PCT/IB2014/063713 filed Aug. 5, 2014, which claims priority to European patent application No. 13170868.7 filed on Jun. 6, 2013. The entire contents of these applications are explicitly incorporated herein by this reference. The present invention relates to a process for the preparation of halogenated carboxylic anhydrides and, more particularly, to a process for the preparation of halogenated carboxylic anhydrides by reacting a halogenated carboxylic acid with sulfuric acid, oleum and/or disulfuric acid.

Halogenated carboxylic anhydrides like trifluoroacetic acid are valuable reagents for the manufacture of various products in the pharmaceutical and agrochemical industry.

It is known to prepare trifluoroacetic anhydride (Hudlicky, Chemistry of Organic Fluorine Compounds, 1976, p. 726) by reaction of trifluoroacetic acid with phosphoric anhydride. The method described therein is disadvantageous for industrial production because phosphoric anhydride is a solid and tends to form amalgams with the reactants and/or products.

Now therefore the invention makes available an improved process for the production of halogenated carboxylic anhydrides. It is an object of the present invention to provide a process for the production of halogenated carboxylic anhydrides allowing for improved yields and/or purity of the products. Furthermore, it is an object of the present invention to provide a process with a more economical and/or more ecological waste and/or unwanted side product profile, e.g. a process wherein the waste and/or side products are more easily separated from the product of the process and/or wherein the waste and/or side products are less toxic and/or less harmful to the environment. Furthermore, it is an object of the present invention to provide a process starting from cheaper, and/or more readily available reactants and/or reagents, as for example using reactants with a lower degree of purity.

These and other objectives are achieved by the process of this invention.

Accordingly, the first embodiment of the present invention is a process for the preparation of a compound of general structure (I):
HalR2C(O)—O—C(O)CR2Hal wherein Hal is selected from the group consisting of F, Cl and Br; and wherein R is independently selected from the group consisting of H, F, Cl, Br, alkyl and aryl; which comprises reacting a compound of general structure (II): HalR2C(O)—OH wherein Hal and R are defined as above, with sulfuric acid, oleum and/or disulfuric acid.

The term "sulfuric acid" is intended to denote pure sulfuric acid, $H_2SO_4$, as well as the aqueous solutions thereof. Preferably, the sulfuric acid used according to this invention has a concentration of 70 wt % and above, more preferably a concentration of 90 wt % and above, and most preferably concentrated sulfuric acid is used, which has a concentration of about 98 wt %.

The term "oleum" is intended to denote mixtures of $H_2SO_4$ and $SO_3$. Concentrations of oleum are either expressed in terms of wt % $SO_3$ (called X % oleum) or as wt % $H_2SO_4$. For example, 65% oleum refers to 114.6 wt % $H_2SO_4$. The percentage of $SO_3$ in the oleum is also referred to as the free $SO_3$. Thus, 65% oleum contains 65 wt % free $SO_3$.

The term "disulfuric acid" is intended to denote $H_2S_2O_7$.

The term "alkyl" is intended to denote an optionally substituted chain of saturated hydrocarbon-based groups, such as, in particular, a C1-C6 alkyl. By way of example, mention may be made of methyl, ethyl, propyl, isopropyl, butyl, t-butyl, pentyl, isopentyl and hexyl.

The term "aryl" is intended to denote an optionally substituted group which derives from an aromatic nucleus such as, in particular, a C6-C10 aromatic nucleus, in particular phenyl or naphthyl.

In a preferred embodiment, Hal is fluorine. More preferably, the compound of general structure (I) is trifluoroacetic anhydride and the compound of general structure (II) is trifluoroacetic acid.

Another embodiment of the present invention is the reaction of acetic acid, an acetate salt or a mixture thereof with sulfuric acid, oleum and/or disulfuric acid to form acetic anhydride. Useful examples of the acetate salt include sodium acetate, potassium acetate, calcium acetate, lithium acetate, magnesium acetate, or any mixtures thereof. The acetate salt and/or the acetic acid can be used in neat form or as a solution in a solvent, preferably as an aqueous solution.

In another preferred embodiment, the compound of general structure (II) is reacted with oleum, preferably the oleum contains from 5 to 95 wt % free $SO_3$, more preferably from 25 to 80 wt % free $SO_3$, most preferably from 50 to 70 wt % free $SO_3$, specifically 65 wt % free $SO_3$.

In another preferred embodiment, the halogenated carboxylic acid is present in molar excess relative to the stoichiometry of the reaction. The total quantity of halogenated carboxylic acid is preferably from 1.05 to 2 times the stoichiometry, more preferably 1.05 to 1.10 times the stoichiometry.

Suitably, the reaction is performed at elevated temperatures, wherein the internal temperature of the reaction mixture is equal to or higher than the boiling point of the product. Preferably, the reaction is performed at a temperature in the reaction mixture from 50 to 150° C., preferably from 70 to 115° C. The temperature of the reaction mixture refers to the internal temperature in the reaction vessel.

In another preferred embodiment, the product is removed from the reaction mixture by distillation, more preferably the distillation is performed using a packing column. The packing column is suitably filled, e.g. with Raschig rings. Also preferably, the distillation is performed using a reflux condenser for controlling the rate at which the product is removed from the reaction mixture.

In another preferred embodiment, the reaction is performed in a reaction vessel which is at least partially ceramic-lined and/or a glass-lined. Suitably, a continuously-stirred Pfaundler vessel with a ceramic lining can be used. Also preferably, the reaction is performed in a reaction vessel at least partially made of an alloy containing nickel and/or molybdenum. Examples of suitable alloys include Hastelloy B, Hastelloy B-2, or Hastelloy B-3.

A further advantage of the process according to the invention is that halogenated carboxylic anhydride of high purity can be produced in high yields even in case of reactants, i.e. the halogenated carboxylic acid, of lower purity are employed. For example, tailing fractions containing unreacted halogenated carboxylic acid and pollutants from previous reactions can be employed in the process of the present invention. Thus, recycled halogenated carboxylic acid can be used in the process of the invention. Accordingly, in a preferred embodiment, the halogenated carboxylic acid employed in the reaction has a purity of equal to or less than 98%, more preferably a purity of less than 95%, even more preferably a purity of less than 90%. Alternatively, the halogenated carboxylic acid employed in the reaction has a purity from 50% to 98%, more preferably a purity from 50% to 95%, even more preferably a purity of 50% to 90%. In another preferred embodiment, the halogenated carboxylic acid used in the process is comprised in a mixture also containing at least one product, at least one reagent, at least one solvent and/or at least one side product from a previous reaction step.

Should the disclosure of any patents, patent applications, and publications which are incorporated herein by reference conflict with the description of the present application to the extent that it may render a term unclear, the present description shall take precedence.

The invention will now be further described in examples without intending to limit it.

EXAMPLES

Production of Trifluoroacetic Anhydride

A 115 l ceramic-lined Pfaundler stirred vessel equipped with a 2.5 m packing column filled with 10 mm glass Raschig rings and equipped with a condenser was filled with 70.5 kg trifluoroacetic acid followed by 19.1 165% oleum, i.e. oleum with 65 wt % free SO3. Subsequently, the Pfaundler vessel was heated by means of an oil bath to a temperature of 130° C. The product was removed by distillation at a rate of 7.4 kg/h and directed into PE-lined metal drums. During the distillation the temperature of the reaction mixture changed gradually from 78° C. to 96° C. The yield of trifluoroacetic anhydride was 64.9 kg (99%). The purity of the product was >99.9%. Additionally, 7.8 kg of a tailing fraction was obtained that contained trifluoroacetic anhydride and trifluoroacetic acid next to other not identified side products. This second fraction can be submitted to the reaction mixture of a subsequent batch.

The invention claimed is:

1. A process for the preparation of trifluoroacetic anhydride, the process comprising reacting trifluoroacetic acid with oleum, wherein the oleum contains from 50 to 65 wt % free $SO_3$.

2. The process of claim 1 wherein the trifluoroacetic acid is present in molar excess relative to the stoichiometry of the reaction.

3. The process of claim 1 wherein the reaction is performed at a temperature in the reaction mixture from 50 to 150° C.

4. The process of claim 1 wherein the trifluoroacetic anhydride is removed from the reaction mixture by distillation.

5. The process of claim 4 wherein the distillation is performed using a packing column.

6. The process of claim 4 wherein the distillation is performed using a reflux condenser for controlling the rate at which the trifluoroacetic anhydride is removed from the reaction mixture.

7. The process of claim 1 wherein the reaction is performed in a reaction vessel which is at least partially ceramic-lined and/or glass-lined.

8. The process of claim 1 wherein the reaction is performed in a reaction vessel at least partially made of an alloy containing nickel and/or molybdenum.

9. The process of claim 1 wherein the trifluoroacetic acid employed in the process has a purity of equal to or less than 98%.

10. The process of claim 1 wherein the trifluoroacetic acid employed in the process is recycled material.

11. The process of claim 1 wherein the trifluoroacetic acid is employed comprised in a mixture containing the trifluoroacetic acid.

12. The process of claim 3 wherein the reaction is performed at a temperature in the reaction mixture from 70 to 115° C.

13. The process of claim 9 wherein the trifluoroacetic acid employed in the process has a purity of less than 95%.

14. The process of claim 13 wherein the trifluoroacetic acid employed in the process has a purity of less than 90%.

* * * * *